(12) United States Patent
Neidle et al.

(10) Patent No.: US 9,145,377 B2
(45) Date of Patent: Sep. 29, 2015

(54) G-QUADRUPLEX STABILISING AGENT

(75) Inventors: Stephen Neidle, London (GB); Caterina Maria Lombardo, London (GB); Sarah Welsh, London (GB)

(73) Assignee: University College London, London (GB)

( * ) Notice: Subject to any disclaimer, the term of this patent is extended or adjusted under 35 U.S.C. 154(b) by 47 days.

(21) Appl. No.: 14/110,315

(22) PCT Filed: Apr. 4, 2012

(86) PCT No.: PCT/GB2012/050757
§ 371 (c)(1),
(2), (4) Date: Dec. 30, 2013

(87) PCT Pub. No.: WO2012/136997
PCT Pub. Date: Oct. 11, 2012

(65) Prior Publication Data
US 2014/0107168 A1    Apr. 17, 2014

(30) Foreign Application Priority Data
Apr. 5, 2011   (GB) .................................. 1105751.0

(51) Int. Cl.
*C07D 249/06*   (2006.01)

(52) U.S. Cl.
CPC .................................... *C07D 249/06* (2013.01)

(58) Field of Classification Search
CPC .................................................... C07D 249/06
See application file for complete search history.

(56) References Cited

FOREIGN PATENT DOCUMENTS

WO    WO-2008/062235 A1    5/2008
WO    WO-2008/122667 A2    10/2008

OTHER PUBLICATIONS

International Search Report in International Application No. PCT/GB2012/050757, filed Apr. 4, 2012.
Moorhouse, A.D., et al., "Stabilization of G-Quadruplex DNA by Highly Selective Ligands via Click Chemistry," Journal of the American Chemical Society, American Chemical Society, vol. 128, No. 50, Dec. 1, 2006, pp. 15972-15973.
Gunaratnam, M., et al., "G-quadruplex compounds and cis-platin act synergistically to inhibit cancer cell growth in vitro and in vivo," Biochemical Pharmacology, vol. 78, No. 2, Jul. 15, 2009, pp. 115-122.
Drewe, W.C., et al., "Click chemistry assembly of G-quadruplex ligands incorporating a diarylurea scaffold and triazole linkers," Chemical Communications, No. 42, 2008, pp. 5295-5297.

*Primary Examiner* — Rebecca Anderson
*Assistant Examiner* — Karen Cheng
(74) *Attorney, Agent, or Firm* — Saliwanchik, Lloyd & Eisenschenk

(57) ABSTRACT

A compound of formula I

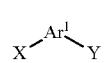

(I)

wherein $Ar^1$ is a bicyclic aryl or heteroaryl, which may be optionally substituted; X and Y are each independently a group of formula II:

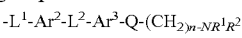

$L^1$ and $L^2$ are each independently selected from $NR^3$, $C_2H_2$, $CH_2$, —O—, —S— and a bond;
$Ar^2$ and $Ar^3$ are independently optionally substituted $C_5$ or $C_6$ aryl or heteroaryl;
Q is selected from $NH(C{=}O)$, $NR^3$, S, O;
n is an integer from 1 to 5;
$R^1$ and $R^2$ are optionally substituted and are independently hydrogen, $C_{1-7}$ alkyl, $C_{3-20}$ heterocyclyl, or $C_{5-20}$ aryl, or $R^1$ and $R^2$, taken together with the nitrogen atom to which they are attached, form a heterocyclic ring having from 3 to 8 ring atoms;
$R^3$ is H or $C_{1-7}$ alkyl.

20 Claims, 7 Drawing Sheets

SEQ ID NO: 400

HIF-1α    5' – GCGCGGGGAGGGGAGAGGGGGCGGGAGCGCG – 3'

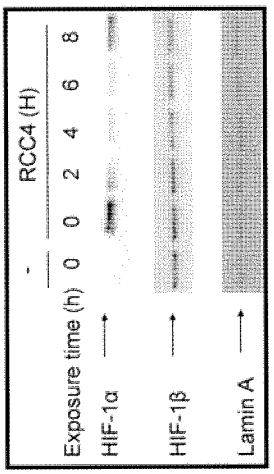
Figure 5(C)
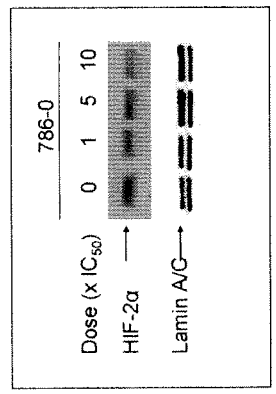
Figure 5(B)
Figure 5
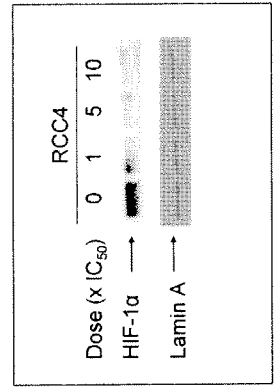
Figure 5(A)

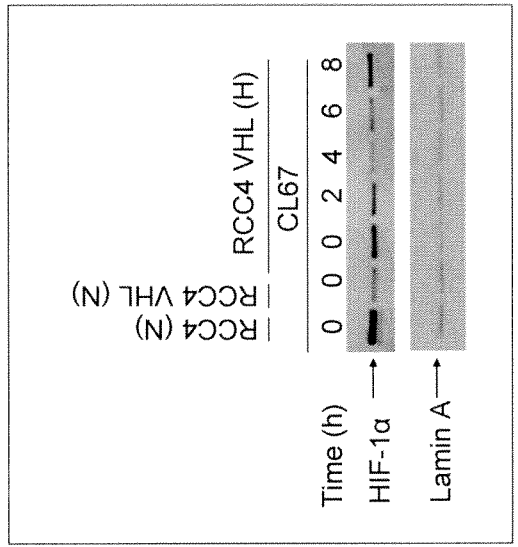
Figure 7(B)
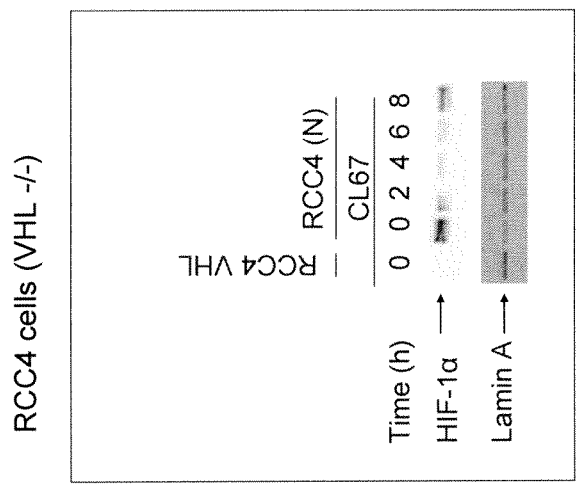
Figure 7(A)
Figure 7

G-QUADRUPLEX STABILISING AGENT

CROSS-REFERENCE TO RELATED APPLICATIONS

This application is the U.S. national stage application of International Patent Application No. PCT/GB2012/050757, filed Apr. 4, 2013, which claims priority to United Kingdom Application No. 1105751.0, filed Apr. 5, 2011.

The present invention relates to compounds which bind G-quadruplexes that can be formed in the promoter region of the HIF gene, and more specifically, to those compounds which stabilise these structures and thereby inhibit the action of the HIF protein. The present invention also relates to pharmaceutical compositions comprising such compounds and their use in the treatment of proliferative conditions, particularly renal cancer.

Hypoxic cancer cells (ie. cells growing in low levels of oxygen) are found in all solid tumours and are very difficult to kill. Hypoxic cells commonly occur when the growth of a tumour outstrips the growth of new blood vessels, but can also occur when abnormal blood vessels are shut down by becoming blocked by tumour cells. Hypoxia-inducible factor (HIF) is a transcription factor that co-ordinates the response of cells to low oxygen levels and is critical for tumour cell survival. In response to low oxygen levels HIF stimulates genes which increase cellular metabolism and cell survival pathways whilst also activating blood vessel growth to improve oxygenation and nourishment. Interestingly, HIF is also independently stimulated, in the absence of hypoxia, by growth factor pathways. HIF is heterodimer consisting of HIF-α and HIF-1β (also known as the aryl hydrocarbon receptor nuclear translocator or ARNT) subunits. There are three alpha isoforms—HIF-1α plays a general role in hypoxia signaling while HIF-2α and HIF-3α show a more restricted pattern of expression. The expression of the HIF pathway is highly regulated, as illustrated in FIG. 1. HIF-α subunits are oxygen-regulated whereas HIF-1β is constitutively expressed. HIF-1α expression has been found to be increased in many human tumours but is absent in most normal tissues. This makes HIF-1α an attractive target for the development of new cancer drugs.

Inhibitors of the HIF pathway are likely to be particularly effective in treating renal cell carcinoma. Loss of the Von Hippel Lindau protein (pVHL) has been shown to lead to elevated HIF-1α and 2α levels [1]. There is a high incidence of renal cell carcinomas in individuals with loss of function of both alleles of the VHL gene. In addition, at least 80% of sporadic renal cell carcinomas have been shown to be associated with an early loss of function of the VHL gene and increased HIF-1α levels [2]. HIF-2α is also commonly up-regulated in renal cancer [3], and may also be important for the growth of other tumor types [4].

Nucleic acid sequences containing several short runs of guanine nucleotides can form complex higher order structures, termed quadruplexes. The highly distinctive nature of quadruplex topologies suggests that they can act as novel therapeutic targets, for example in the selective inhibition of transcription of a given oncogene, using designed small molecules to stabilise a particular quadruplex. The promoters of both HIF-1α and HIF-2α contain a number of guanine-rich sequences capable of forming G-quadruplex structures which can modulate the activity of the HIF-1α promoter (see FIG. 2) [5].

In our previous patent application, published as WO2008/062235, we have described compounds with a monocyclic core which act as selective G-quadruplex ligands. These compounds were shown to inhibit the action of the enzyme telomerase. We have also shown that acridine-based ligands can have selectivity for human telomeric quadruplexes [10].

In accordance with a first aspect of this invention, we provide a compound of formula I:

(I)

wherein $Ar^1$ is a bicyclic aryl or heteroaryl which is optionally substituted;

X and Y are each independently a group of formula II:

(II)

$L^1$ and $L^2$ are each independently selected from $NR^3$, $C_2H_2$, $CH_2$, —O—, —S— and a bond;

$Ar^2$ and $Ar^3$ are independently optionally substituted $C_5$ or $C_6$ aryl or heteroaryl;

Q is selected from $NHC(=O)$, $NR^3$, S, O;

n is an integer from 1 to 5;

$R^1$ and $R^2$ are optionally substituted and are independently hydrogen, $C_{1-7}$ alkyl, $C_{3-20}$ heterocyclyl, or $C_{6-20}$ aryl, or $R^1$ and $R^2$, taken together with the nitrogen atom to which they are attached, form a heterocyclic ring having from 3 to 8 ring atoms; and $R^3$ is H or $C_{1-7}$ alkyl.

These compounds form part of a planar pharmacophore that is capable of π-stacking interactions with the G-quadruplex structures in the HIF promoter region. The group of formula (II) may advantageously bind the quadruplex. The compounds are selective for quadruplex structures in HIF and thus can be used to selectively target renal cell carcinomas. The compounds described previously in WO 2008/062235 are not selective for such carcinomas. Conventional treatments for renal cancer can be both toxic and non-selective. The present invention may avoid the toxicity problems of the anti-cancer compounds of the prior art.

In accordance with a second aspect of the invention we provide a compound according to the first aspect of the invention for use in the treatment of a proliferative condition, preferably cancer, and most preferably renal cancer.

A third aspect of the invention relates to a method of inhibiting the HIF pathway in vitro or in vivo, comprising contacting a cell with an effective amount of compound according to the first aspect of the invention.

A fourth aspect of the invention relates to a method of regulating cell proliferation in vitro or in vivo, comprising contacting a cell with an effective amount of compound according to the first aspect of the invention.

A fifth aspect of the invention relates to a method for the treatment of a proliferative condition comprising administering to a subject suffering from said proliferative condition a therapeutically effective amount of a compound according to the first aspect of the invention; wherein the proliferative condition is preferably cancer, most preferably renal cancer.

The compounds according to the first aspect of this invention are ideally manufactured using "click chemistry". The concept of click chemistry, originally conceived by Barry K. Sharpless makes use of "near perfect" reactions in order to bring about reliable transformations and provide rapid access to large areas of chemical space. The Cu(I) catalysed Huisgen cycloaddition in particular has proven to be a very useful ligation reaction in fragment based drug discovery. In these applications the clicked triazole acts as a reliable sturdy linkage which can be formed selectively between a complimentary azide and alkyne pair, in good yield and without the need for purification. This approach offers a reliable and efficient method for manufacturing the novel compounds of the invention.

Certain compounds and combinations of substituents are preferred, in particular see the sub-claims. With regard to the structural preferences, a planar core with a π-delocalised system enables stacking on the face of a guanine quartet. Side chain groups which may be protonated are preferred, since these provide stabilising interactions with the sugar-phosphate loops of the G-quadruplex, facilitating stacking of the compound with the quadruplex. Amine side chain groups typically have suitable $pK_B$ values for protonation at physiological pH. The $pK_B$ value is typically in the range 6.5-8.5.

The term "hetero" as used herein refers to compounds and/or groups which have at least one heteroatom, for example boron, silicon, nitrogen, phosphorus, oxygen and sulphur (multivalent heteroatoms), and fluorine, chlorine, bromine and iodine (monovalent heteroatoms). Preferably the heteroatom is nitrogen.

The term "bicyclic aryl or heteroaryl" as used herein refers to cyclic compounds which have two fused aromatic rings, which may contain one or more multivalent heteroatoms in the case of bicyclic heteroaryl.

The phrase "optionally substituted" as used herein refers to a parent group which may be substituted or unsubstituted.

Unless otherwise specified, the term "substituted", as used herein, refers to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

Suitably, the substituent(s) are independently selected from: halo; hydroxy; ether (e.g., $C_{1-7}$ alkoxy); formyl; acyl (e.g., $C_{1-7}$ alkylacyl, $C_{5-20}$ arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$ alkylthio); sulfonic acid; sulfonate; sulfone; sulfonyloxy; sulfinyloxy; sulfamino; sulfonamino; sulfinamino; sulfamyl; sulfonamido; $C_{1-7}$ alkyl (including, e.g. $C_{1-7}$ haloalkyl, $C_{1-7}$ hydroxyalkyl, $C_{1-7}$ carboxyalkyl, $C_{1-7}$ aminoalkyl, $C_{5-20}$ aryl-$C_{1-7}$ alkyl); $C_{3-20}$ heterocyclyl; or $C_{5-20}$ aryl (including, e.g., $C_{5-20}$ aryl, $C_{5-20}$ heteroaryl, $C_{1-7}$ alkyl-$C_{5-20}$ aryl and $C_{5-20}$ haloaryl)).

More specifically, the substituents may be selected from:
—F, Cl, —Br, and —I;
—OH;
—OMe, —OEt, —O(tBu), and —OCH$_2$Ph;
—SH;
—SMe, —SEt, —S(tBu), and —SCH$_2$Ph;
—C(=O)H;
—C(=O)Me, —C(=O)Et, —C(=O)(tBu), and —C(=O)Ph;
—C(=O)OH;
—C(=O)OMe, —C(=O)OEt, and —C(=O)O(tBu);
—C(=O)NH$_2$, —C(=O)NHMe, —C(=O)NMe$_2$, and —C(=O)NHEt;
—NHC(=O)Me, —NHC(=O)Et, —NHC(=O)Ph, succinimidyl, and maleimidyl;
—NH$_2$, —NHMe, —NHEt, —NH(iPr), —NH(nPr), —NMe$_2$, —NEt$_2$, —N(iPr)$_2$, —N(nPr)$_2$, —N(nBu)$_2$, and —N(tBu)$_2$;
—CN;
—NO$_2$;
-Me, -Et, -nPr, -iPr, -nBu, -tBu;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$;
—CH$_2$OH, —CH$_2$CH$_2$OH, and —CH(OH)CH$_2$OH;
—CH$_2$NH$_2$, —CH$_2$CH$_2$NH$_2$, and —CH$_2$CH$_2$NME$_2$; and, optionally substituted phenyl.

With regard to the compound of formula I, it is preferred that Ar$^1$ is bicyclic aryl which is unsubstituted, preferably naphthalene. Multicyclic ring systems are known to bind to duplex DNA. It is thought that the bicyclic aryl ring Ar$^1$ gives specificity for certain cancers, particularly renal cancer. In this embodiment, preferably X and Y are substituted 2,7 on the naphthalene ring. By this is meant the following arrangement:

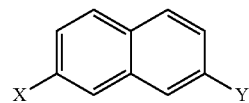

There may be one or more substituents, Z, on the Ar$^1$ ring. The optional substituents Z are typically selected from $C_{1-4}$ alkyl, halo or $C_1$ alkoxy. For instance Z may be F, methyl, ethyl, OMe or OEt.

Although X and Y may be different, they are preferably the same.

Examples of suitable heteroaryl groups for Ar$^2$ and Ar$^3$ include, but are not limited to, those derived from pyrrole, pyridine, furan, thiophene, oxazole, isoxazole, isoxazine, oxadiazole, oxatriazole, thiazole, isothiazole, imidazole, pyrazole, pyridazine, pyrimidine, pyrazine, triazole, triazine and tetrazole. Preferably, each Ar$^2$ is triazole. Preferably Ar$^3$ is phenyl.

Further preferred compounds are those of formula I wherein one or both of L$^1$ and L$^2$ is a bond.

Preferably, in compounds of the invention, Q is NH(C=O).

In preferred embodiments, R$^1$ and R$^2$ are each independently $C_{1-7}$ alkyl, typically $C_{1-4}$ alkyl which is optionally substituted. Preferably, each —NR$^1$R$^2$ is independently selected from —N(Me)$_2$, —N(Et)$_2$, —N(nPr)$_2$, —N(iPr)$_2$, —N(nBu)$_2$ and —N(tBu)$_2$.

Alternatively, R$^1$ and R$^2$, together with the nitrogen atom to which they are attached, form a heterocyclic ring having from 3 to 8 ring atoms, which heterocyclic ring may saturated, partially unsaturated, or fully unsaturated, and is optionally substituted. In one preferred embodiment, preferably R$^1$ and R$^2$, taken together with the nitrogen atom to which they are attached, form a saturated heterocyclic ring having from 3 to 8 ring atoms, wherein only one of said ring atoms is nitrogen, and all others are carbon, and which heterocyclic ring is optionally substituted. In these embodiments R$^1$ and R$^2$, taken together with the nitrogen atom to which they are attached may form a cyclic amino group of the following formula, wherein q is an integer from 2 to 7, and wherein said group is optionally substituted:

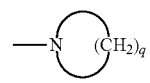

Suitable, and particularly preferred terminal amino groups include the following cyclic amino groups, which may be optionally substituted:

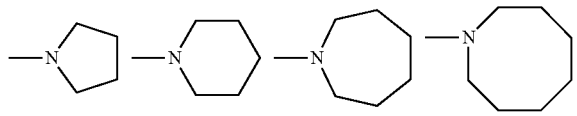

This cyclic amino group may be substituted with one or more substituents selected from $C_{1-7}$ alkyl, $C_{3-20}$ aryl, hydroxy, and $C_{1-7}$ hydroxyalkyl.

Alternatively, each —$NR^1R^2$ may be independently selected from

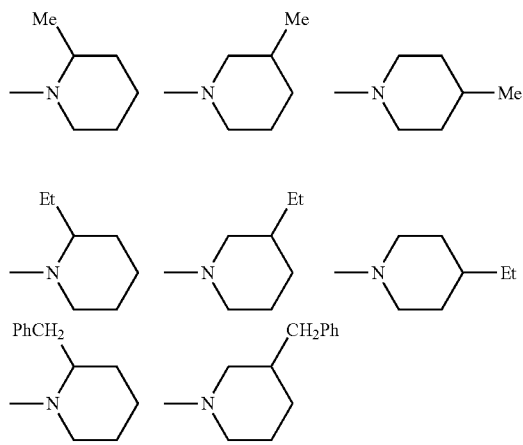

-continued

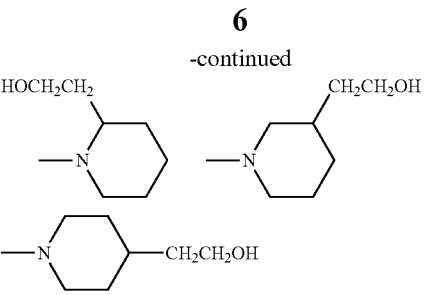

In other preferred embodiments, $R^1$ and $R^2$, taken together with the nitrogen atom to which they are attached, form a saturated heterocyclic ring having from 3 to 8 ring atoms, wherein said ring has at least two heteroatoms selected from nitrogen, oxygen, and sulfur, which heterocyclic ring is optionally substituted.

It is preferred in this embodiment that the terminal amino group, —$NR^1R^2$, is one of the following cyclic amino groups, and is optionally substituted:

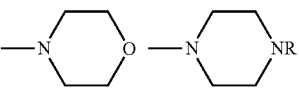

wherein R is hydrogen, $C_{1-7}$alkyl, $C_{3-20}$heterocyclyl, or $C_{5-20}$aryl.

In the preferred compounds of the invention, n is typically in the range 1-3 and is preferably 1 or 2, most preferably 2. $R^3$ is preferably $C_{1-4}$ alkyl.

Some individual embodiments of the present invention include compounds of formula

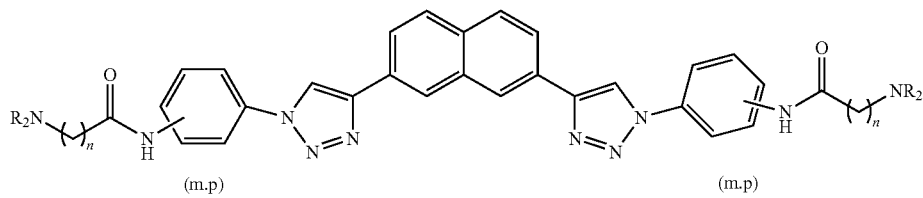

wherein n is 1 or 2; and each R is $C_{1-4}$ alkyl (preferably $C_{1-2}$ alkyl), $C_{4-5}$ heterocyclyl or $C_{3-5}$ heteroaryl, or the two R groups attached to each nitrogen, taken together with the nitrogen to which they are attached, form a heterocyclic ring having 5-7 ring atoms.

"m" and "p" mean that the substituents can be arranged meta and para on the phenyl ring respectively.

In these compounds, the terminal amino group is preferably one of the following amino groups, and is optionally substituted:

The following compounds are particularly preferred:
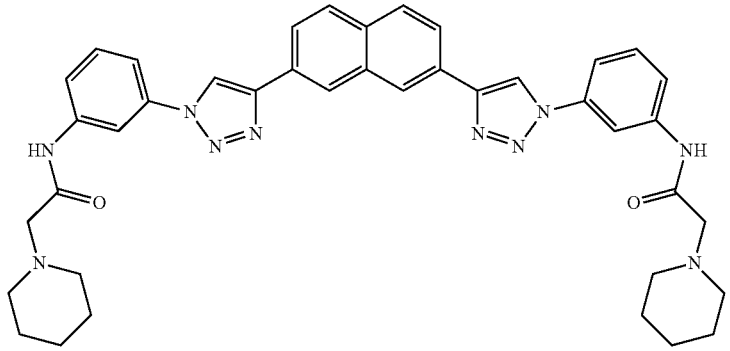
CL61
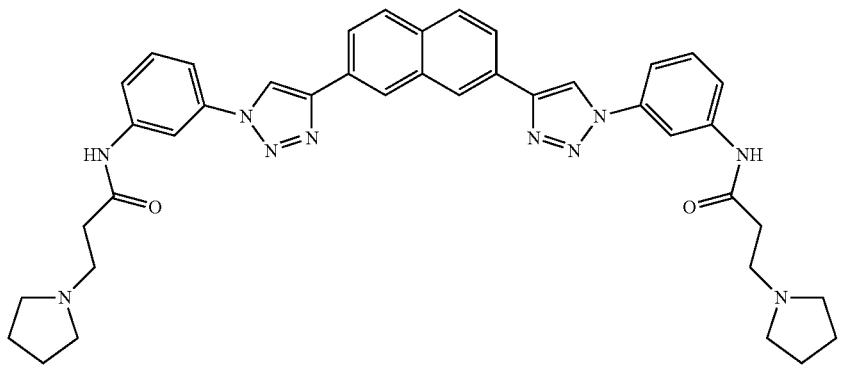
CL62
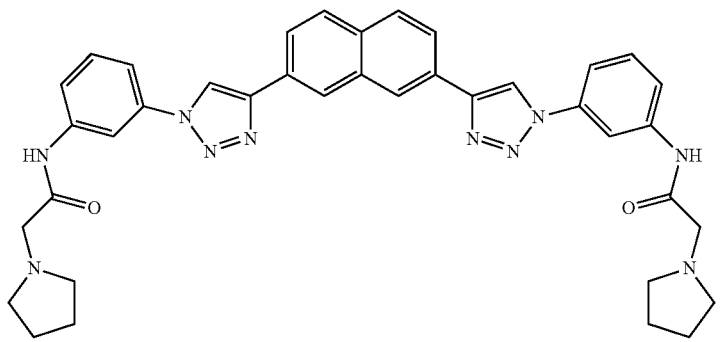
CL63
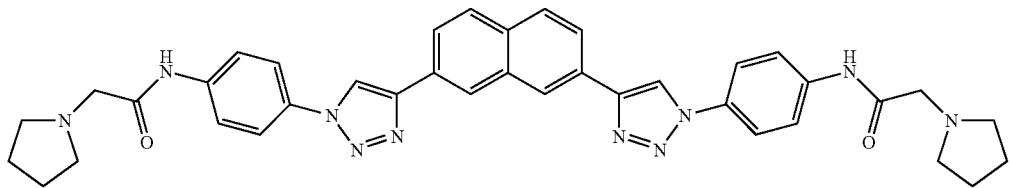
CL64
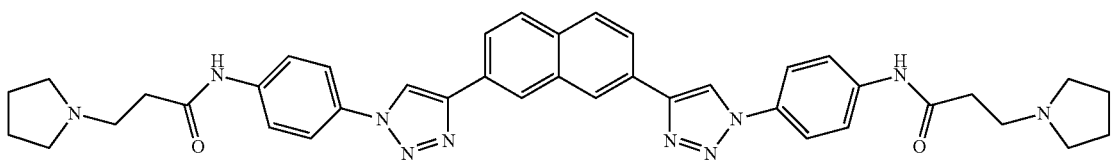
CL65

CL66
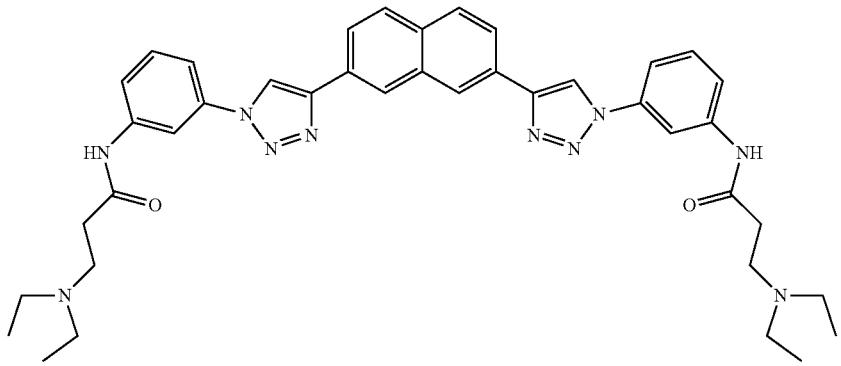

CL67
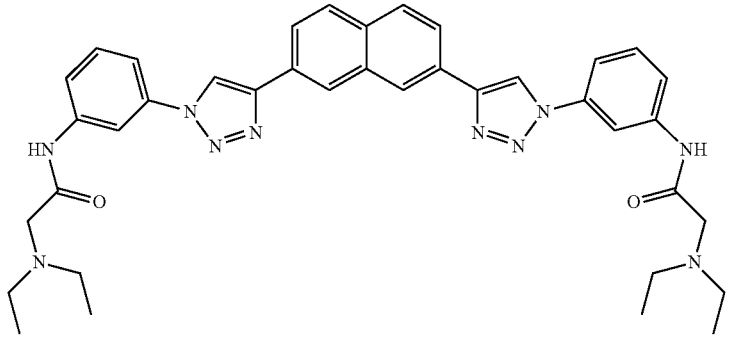

CL68
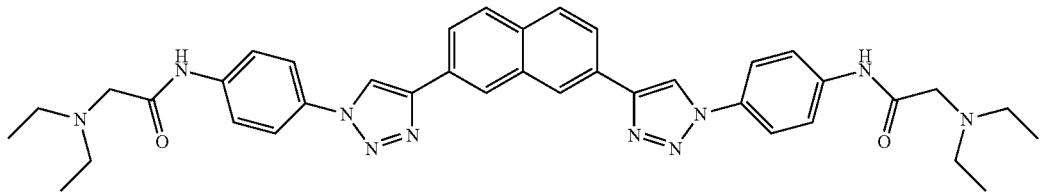

CL70
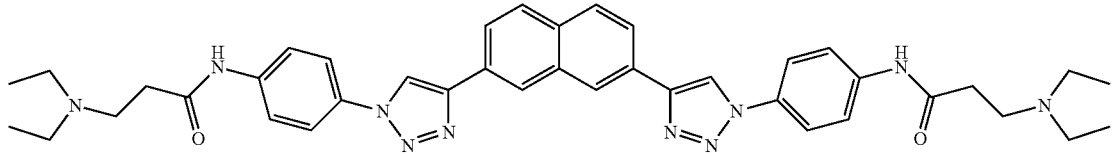

Compounds of the invention may be chiral. They may be in the form of a single enantiomer or diastereomer, or a racemate.

Chiral compounds of the invention may be prepared in racemic form, or prepared in individual enantiomeric form by specific synthesis or resolution as will be appreciated by the person skilled in the art. The compounds may, for example, be resolved into their enantiomers by standard techniques, such as the formation of diastereomeric pairs by salt formation with an optically active acid followed by fractional crystallisation and regeneration of the free base. Alternatively, the enantiomers of the novel compounds may be separated by HPLC using a chiral column.

A compound of the invention may be in a protected amino, protected hydroxy or protected carboxy form. The terms "protected amino", "protected hydroxy" and "protected carboxy" as used herein refer to amino, hydroxy and carboxy groups which are protected in a manner familiar to those skilled in the art. For example, an amino group can be protected by a benzyloxycarbonyl, tert-butoxycarbonyl, acetyl or like group, or in the form of a phthalimido or like group. A carboxyl group can be protected in the form of a readily cleavable ester such as the methyl, ethyl, benzyl or tert-butyl ester. A hydroxy group can be protected by an alkyl or like group.

Some compounds of formula I may exist in the form of solvates, for example hydrates, which also fall within the scope of the present invention.

Compounds of the invention may be in the form of pharmaceutically acceptable salts, for example, addition salts of inorganic or organic acids. Such inorganic acid addition salts include, for example, salts of hydrobromic acid, hydrochloric acid, nitric acid, phosphoric acid and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1,2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4- hydroxybenzoyl)benzoic acid, 1-hydroxy-2-naphthoic acid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulphuric acid, mucic acid, 2-naphthalenesulphonic acid, pamoic acid, pantothenic acid, phosphanilic acid ((4-aminophenyl)phosphonic acid), picric acid, salicylic acid, stearic acid, succinic acid, tannic acid, tartaric acid, terephthalic acid, p-toluenesulphonic acid, 10-undecenoic acid and the like.

Salts may also be formed with inorganic bases. Such inorganic base salts include, for example, salts of aluminium, bismuth, calcium, lithium, magnesium, potassium, sodium, zinc and the like. Organic base salts include, for example, salts of N, N'-dibenzylethylenediamine, choline (as a counterion), diethanolamine, ethanolamine, ethylenediamine, N,N'-bis(dehydroabietyl)ethylenediamine, N-methylglucamine, procaine, tris(hydroxymethyl)aminomethane ("TRIS") and the like.

It will be appreciated that such salts, provided that they are pharmaceutically acceptable, may be used in therapy. Such salts may be prepared by reacting the compound with a suitable acid or base in a conventional manner.

The compounds of the invention may be used in the treatment of numerous conditions, the cause of which is linked to unregulated cell division. The present invention provides compounds which are antiproliferative agents. The term "antiproliferative agent" as used herein is a compound which is useful in the treatment of a proliferative condition. The invention may also be used in other human diseases in which the HIF pathway is involved, such as rheumatoid arthritis, anemia and diabetes.

The terms "cell proliferation", "proliferative condition", "proliferative disorder", and "proliferative disease", are used interchangeably herein and refer to an unwanted or uncontrolled cellular proliferation of excessive or abnormal cells which is undesired, such as, neoplastic or hyperplastic growth, whether in vitro or in vivo. Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g. ovarian carcinoma, breast carcinoma, bowel cancer, colon cancer, renal cancer, lung cancer, small cell lung cancer, testicular cancer, prostate cancer, sarcoma, osteosarcoma, Kaposi's sarcoma, melanoma), leukemias, psoriasis, bone diseases, fibroproliferative disorders (e.g. of connective tissues), and atherosclerosis. Any type of cell may be treated, including but not limited to, colon, kidney (renal), breast (mammary), lung, ovarian, liver (hepatic), pancreas, skin, and brain.

Antiproliferative compounds of the present invention have application in the treatment of cancer, and so the present invention further provides anticancer agents. The term "anticancer agent" as used herein, refers to a compound which treats a cancer (i.e., a compound which is useful in the treatment of a cancer). The anti-cancer effect may arise through inhibition of the HIF pathway. The compounds of the invention have been shown to be selective against renal cell lines and may therefore be particularly suited to the treatment of renal cancer.

The invention further provides active compounds for use in a method of treatment of the human or animal body, for example, in the treatment of a proliferative condition, for example cancer. Such a method may comprise administering to such a subject a therapeutically-effective amount of an active compound, preferably in the form of a pharmaceutical composition.

The term "treatment", as used herein in the context of treating a condition, refers generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount", as used herein, refers to that amount of an active compound, or a material, composition or dosage form comprising an active compound, which is effective for producing some desired therapeutic effect, commensurate with a reasonable benefit/risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g. drugs, antibodies (e.g., as in immunotherapy), prodrugs (e.g. as in photodynamic therapy, GDEPT, ADEPT, etc)); surgery; radiation therapy; and gene therapy.

Suitable routes of administration, dosage levels, and pharmaceutical forms are outlined in WO 2008/062235.

A compound of the invention may be prepared by any suitable method known in the art. Suitable methods are given in the Examples.

"Click" chemistry may be used to synthesise the compounds of the invention. Triazole units are suitably synthesised using the Cu(I) catalysed Huisgen cycloaddition as detailed in the examples. It has been found that reaction yield is maximised when an alcohol and water are added to the reaction mixture, and used as solvents for the reaction.

Particularly preferable conditions are a 1:1 mixture of $^t$BuOH:H$_2$O with CuSO$_4$.5H$_2$O and sodium ascorbate. Stirring at room temperature may be sufficient for the reaction to proceed for some starting compounds. Alternatively, microwave radiation may be needed to drive the reaction to completion.

Tetrazole units may be synthesised using a nitrile as shown in the following reaction scheme:

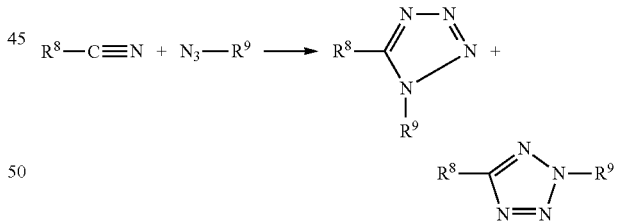

Instead of a cyanide, alternative reagents may be used such as R$^8$C≡S or an isonitrile.

The invention is illustrated further with reference to the following figures, in which FIG. 1 shows the HIF pathway;

Figure 6:
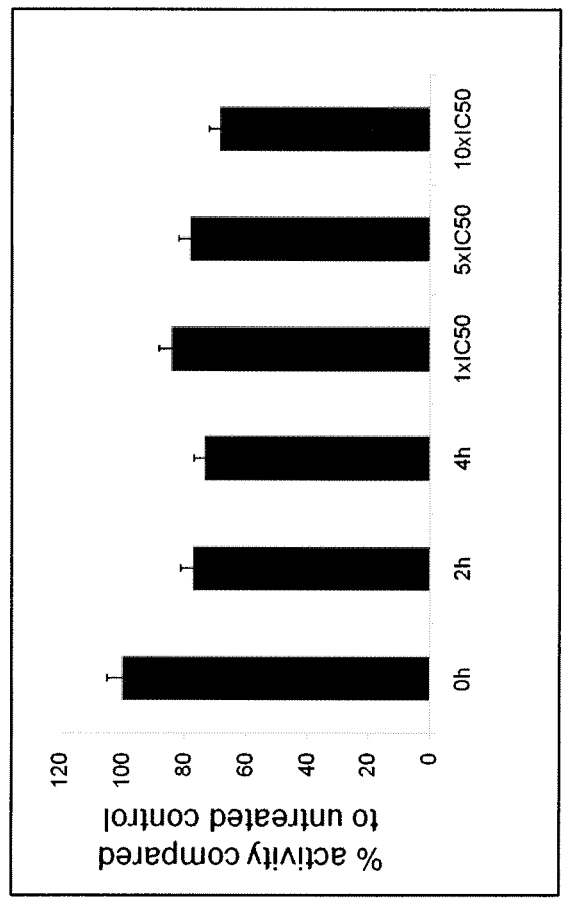
Figure 6:
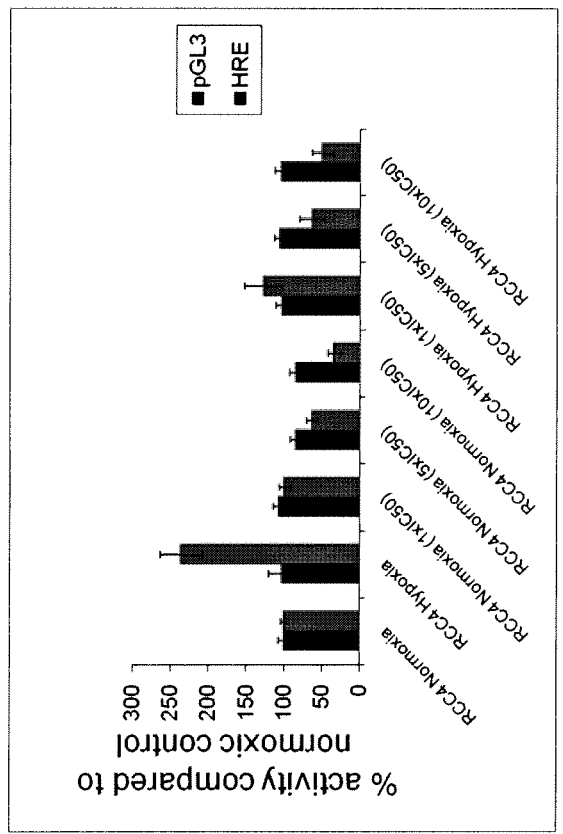
Figure 8:
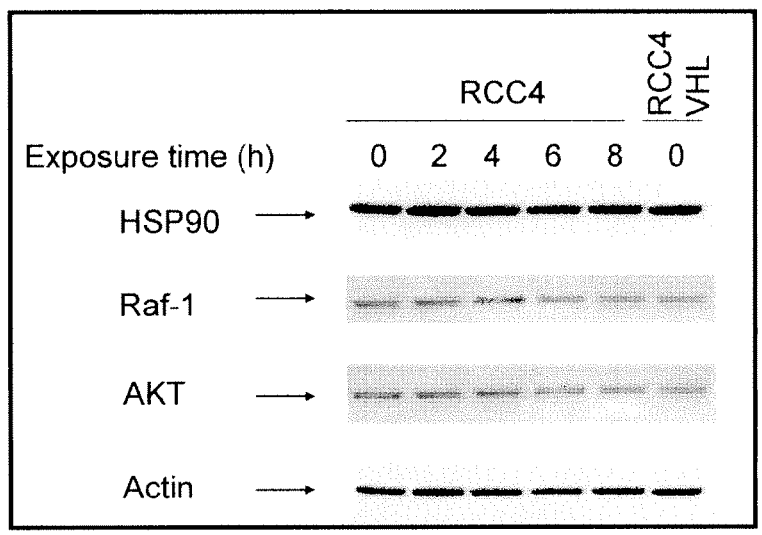

FIG. 5 illustrates how CL67 inhibits HIF-1 α and HIF-2 α protein in a dose and time dependent manner; (FIG. 5A—HIF-1 α dose course; FIG. 5B—HIF-2 α dose course; FIG. 5C—Time course);

FIG. 6 illustrates how CL67 inhibits HIF-1 transactivation and down-stream target genes; (FIG. 6A—HIF-1 transactivation; FIG. 6B—VEGF levels);

FIG. 7 illustrates how CL67 inhibits HIF-1α in a PVHL independent manner;

FIG. 8 illustrates further effects of CL67 on the HIF pathway; and

Figure 9:
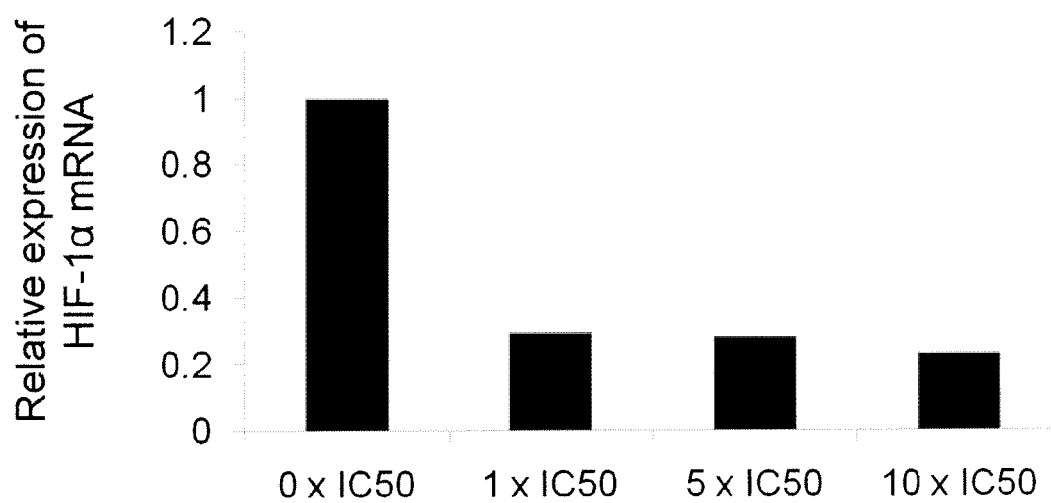

FIG. 9 illustrates how CL67 inhibits HIF-1α by inhibiting transcription of HIF-1α.

The following examples illustrate the invention.

EXAMPLES

Materials and Methods

Example 1

Figure 1:
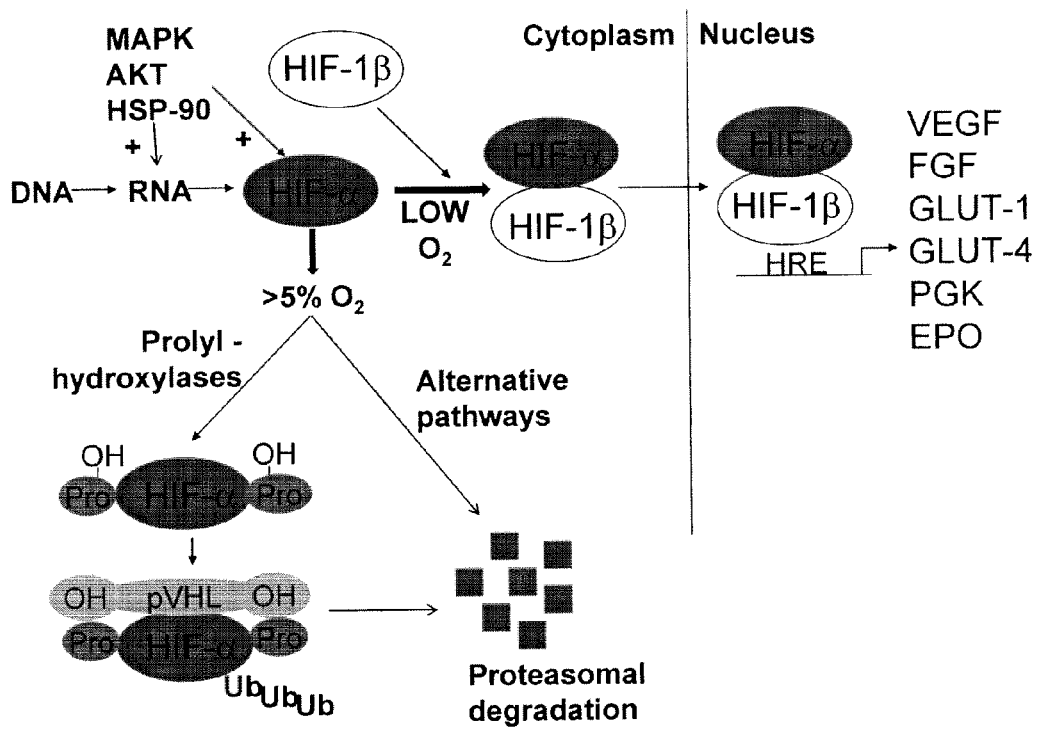
Figures 2, 3:
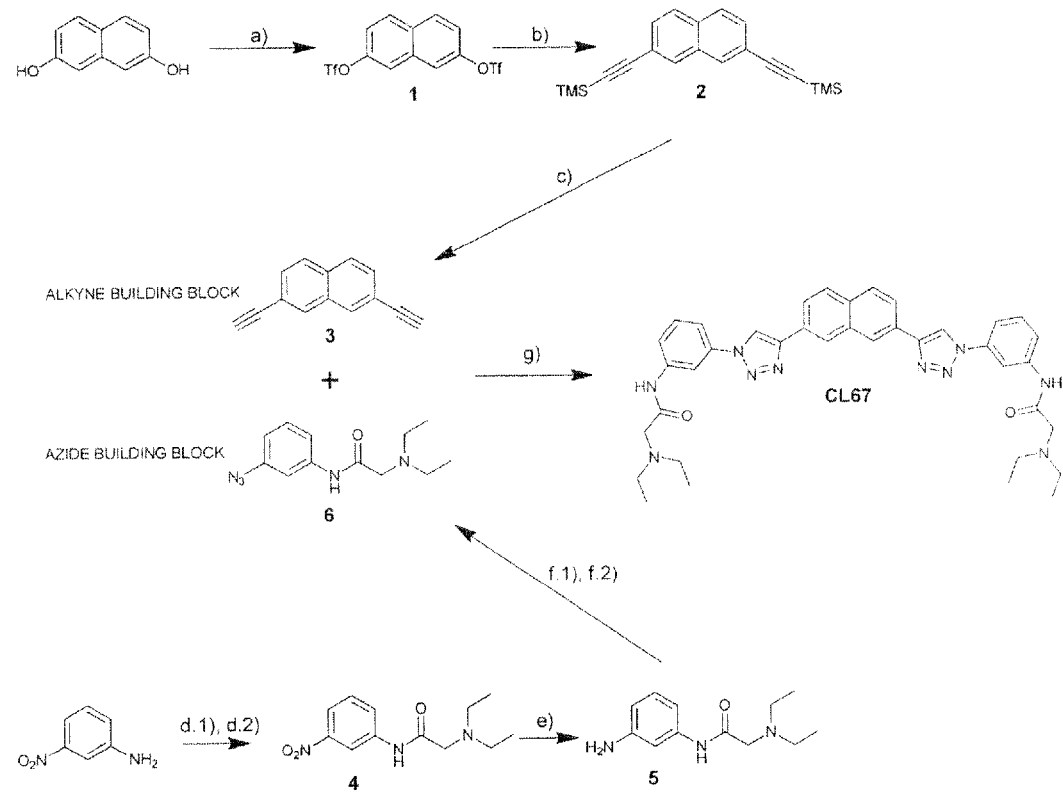
FIG. 2 shows the G-quadruplex forming sequence of the HIF-1α gene.
FIG. 3 shows the synthesis of compound CL67.

The overall reaction synthesis of CL67 is shown in FIG. 3.

Reaction conditions: a) Tf$_2$O, DMAP, 2,6-lutidine, anhydrous THF, anhydrous DCM, molecular sieves, Ar, −78° C. 2 hours, 0° C. 5 hours; b) Ethynyltrimethylsilane, CuI, Pd(PPh$_3$)$_4$, PPh$_3$, piperidine, molecular sieves, Ar, reflux overnight; c) NaOH 1M in H$_2$O, THF, rt, 2 hours; d.1) TEA, acetyl chloride, THF, 4° C. to rt, 2.5 hours; d.2) diethylamine, 4° C. to rt, overnight; e) H$_2$, Pd/C, anhydrous THF, N$_2$, rt, overnight; f.1) HCl (conc.), $^t$BuONO, THF, 4° C., 1.5 hours; f. 2) NaN$_3$, H$_2$O, 4° C. to rt, overnight; g) CuSO$_4$.5H$_2$O, sodium ascorbate, bathophenanthrolinedispufonic acid disodium salt hydrate, 50% H$_2$O-50% $^t$BuOH, microwave irradiation, 110° C., 15 minutes.

Example 1a

Synthesis of Alkyne Building Block

Procedure for the synthesis of naphthalene-2,7-diyl bis(trifluoromethanesulfonate) (1)

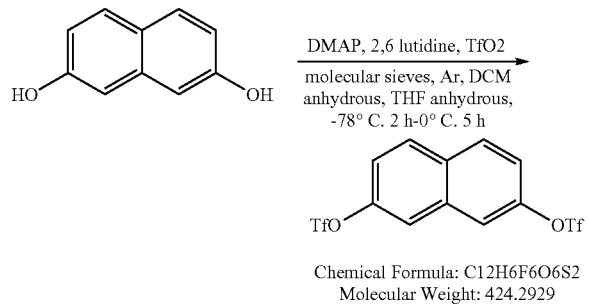

Chemical Formula: C12H6F6O6S2
Molecular Weight: 424.2929

A mixture of 2,7-dihydroxynaphthalene (3.00 g, 18.73 mmol), DMAP (0.42 g, 3.75 mmol) and 2,6-lutidine (4.41 g, 41.18 mmol) was suspended in anhydrous DCM (30 ml) and anhydrous THF (30 ml) in the presence of molecular sieves under an Ar$_2$ atmosphere at −78° C. Tf$_2$O (11.10 g, 39.33 mmol) was added dropwise to this stirred mixture over 15 minutes and the reaction was stirred at −78° C. for 2 hours, then for 5 hours at 0° C. After that time, the reaction was carefully neutralised with saturated aqueous NaHCO$_3$ solution (70 ml), extracted with DMC (6×120 ml), dried (MgSO$_4$), filtered and the solvent removed in vacuo. The orange oil thus obtained was purified by flash column chromatography (petroleum ether:EtOAc, 95:5) to give compound 1 as a white solid (4.94 g, 62%); Rf 0.27 [5% EtOAc in petroleum ether]; mp 60-62° C.; δ$_H$ (CDCl$_3$, 400 MHz) 7.92 (2H, d, J=9.2 Hz, 2×ArH), 7.73 (2H, d, J=2.4 Hz, 2×ArH), 7.40 (2H, dd, J$_1$=8.8 Hz, J$_2$=2.4 Hz, 2×ArH); δ$_C$ (CDCl$_3$, 100 MHz) 148.26 (2×Ar—C), 133.62 (Ar—C), 131.27 (Ar—C), 130.80 (2×Ar—CH), 121.13 (2×Ar—CH), 119.48 (2×Ar—CH), 118.77 (2×CF$_3$); HRMS m/z calc. C$_{12}$H$_6$F$_6$O$_2$S$_2$Na [M+Na]$^+$446.9408. found [M+Na]$^+$446.9424; anal.CHN calcd. C$_{12}$H$_6$F$_6$O$_2$S$_2$ C, 34.0%; H, 1.4%. found C, 34.2%; H, 1.2%. Spectroscopic data are in accordance with those reported in literature (Yao et al., 1998).

Procedure for the synthesis of 2,7-bis((trimethylsilyl)ethynyl)naphthalene (2)

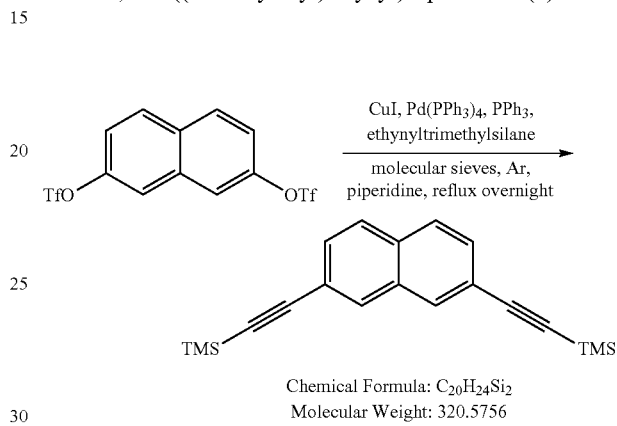

Chemical Formula: C20H24Si2
Molecular Weight: 320.5756

A mixture of naphthalene-2,7-diyl bis(trifluoromethanesulfonate) 1 (1.00 g, 1.19 mmol), CuI (0.023 g, 0.12 mmol), Pd(PPh$_3$)$_4$ (0.14 g, 0.12 mmol) and PPh$_3$ (0.062 g, 0.24 mmol) was dissolved in piperidine (30 ml) in the presence of molecular sieves and under an Ar$_2$ atmosphere. Ethynyltrimethylsilane (0.69 g, 7.06 mmol) was added and the stirred mixture heated at reflux overnight. The solvent was evaporated in vacuo and the resulting brown oil purified by flash column chromatography (5% EtOAc in hexane). 2,7-bis((trimethylsilyl)ethynyl)naphthalene 2 was obtained as a colourless solid (0.69 g, 90%); Rf 0.37 [3% EtOAc in hexane]; mp: 127-129° C. (Lit. 62.5° C., Crisp et al., 1997); δ$_H$ (CDCl$_3$, 400 MHz) 7.91 (2H, s, 2×ArH), 7.71 (2H, d, J=8.4 Hz, 2×ArH), 7.50 (2H, m, 2×ArH), 0.28 (18H, m, 6×CH$_3$Si); δ$_C$ (CDCl$_3$, 100 MHz) 132.34 (Ar—C), 132.26 (Ar—C), 131.64 (2×Ar—CH), 129.48 (2×Ar—CH), 127.70 (2×Ar—CH), 121.17 (2×Ar—C), 105.01 (2×C≡C), 95.17 (2×C≡C), −0.03 (6×CH$_3$Si); HRMS m/z calc. C$_{20}$H$_{25}$Si$_2$ [M+H]$^+$321.1495. found [M+H]$^+$321.1499; anal.CHN calcd. C$_{20}$H$_{25}$Si$_2$ C, 74.9%; H, 7.5%. found C, 74.6%; H, 7.5%.

Procedure for the synthesis of 2,7-diethynylnaphthalene (3)

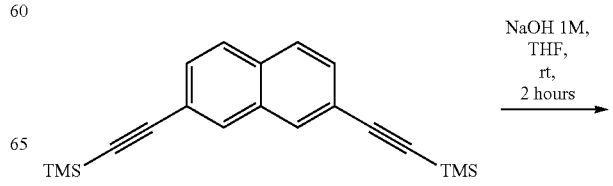

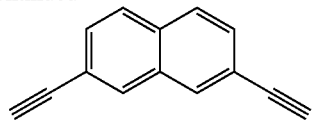

Chemical Formula: $C_{14}H_8$
Molecular Weight: 176.2133

2,7-bis((Trimethylsilyl)ethynyl)naphthalene 2 (0.45 g, 1.39 mmol) was dissolved in THF (80 ml) and aqueous 1M NaOH solution (80 ml) and the mixture stirred for two hours at room temperature. The reaction was extracted with DCM (3×250 ml), dried (MgSO$_4$) and taken to dryness in vacuo. The pale yellow crude solid obtained was purified by flash column chromatography (hexane), to give 2,7-diethynyl-naphthalene 3 (0.24 g, quantitative) as an off white solid; Rf 0.56 [5% EtOAc in hexane]; mp: 124-126° C.; $\delta_H$ (CDCl$_3$, 400 MHz) 7.97 (2H, s, 2×ArH), 7.76 (2H, d, J=8.8 Hz, 2×ArH), 7.54 (2H, dd, J$_1$=8.4 Hz, J$_2$=1.6 Hz, 2×ArH), 3.17 (2×HC≡C); $\delta_C$ (CDCl$_3$, 100 MHz) 132.57 (Ar—C), 132.30 (Ar—C), 132.00 (2×Ar—CH), 129.58 (2×Ar—CH), 127.90 (2×Ar—CH), 120.33 (2×Ar—C), 83.57 (2×C≡C), 77.99 (2×HC≡C); HRMS m/z calc. C$_{14}$H$_8$ [M]$^+$176.0620. found [M+H]$^+$176.0625; anal. CHN calcd. C$_{14}$H$_8$ C, 95.4%; H, 4.6%. found C, 95.3%; H, 4.3%.

Example 1b

Synthesis Of Azide Building Block Procedure for the synthesis of 2-(diethylamino)-N-(3-nitrophenyl)acetamide (4)

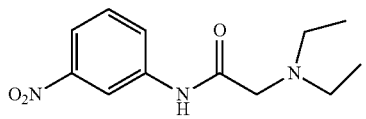

Chemical Formula: $C_{12}H_{17}N_3O_3$
Molecular Weight: 251.2817

A solution of 3-nitroaniline (1.00 g, 7.24 mmol) in THF (20 ml) was cooled to 4° C. in an ice bath. To this stirred mixture TEA (1.47 g, 14.50 mmol), then chloroacetyl chloride (0.98 g, 8.70 mmol) were sequentially added. The reaction was allowed to warm up to room temperature and after 2 and a half hours diethylamine (1.59 g, 21.7 mmol) was added in ice bath and the resulting mixture stirred overnight at room temperature. After completion (TLC 5% MeOH in DCM), solvent was evaporated in vacuo. The crude product was dissolved in DCM (75 ml), washed 3 times with saturated aqueous NaHCO$_3$ solution (50 ml), dried (MgSO$_4$), filtered and taken to dryness in vacuo. The crude product thus obtained was purified by flash column chromatography (0%-5% MeOH in DCM) to give 2-(diethylamino)-N-(3-nitrophenyl)acetamide 4 as a yellow semi-solid (0.92 g, 50%); Rf 0.26 [5% MeOH in DCM]; $\delta_H$ (CDCl$_3$, 400 MHz) 9.68 (1H, s, NH), 8.36-8.35 (1H, m, ArH), 8.05-8.03 (1H, m, ArH), 7.93 (1H, dd, J$_1$=8.4 Hz, J$_2$=1.6 Hz, ArH), 7.51-7.57 (1H, m, ArH), 3.18 (2H, s, CH$_2$), 2.67 (4H, quartet, J=7.2 Hz, 2×CH$_2$), 1.10 (6H, t, J=7.2 Hz, 2×CH$_3$); $\delta_C$ (CDCl$_3$, 100 MHz) 169.95 (C=O), 147.27 (Ar—C), 138.64 (Ar—C), 129.61 (Ar—CH), 110.74 (Ar—CH), 109.17 (Ar—CH), 105.92 (Ar—CH), 58.14 (CH$_2$), 48.79 (2×CH$_2$), 12.39 (2×CH$_3$); LC-MS (5 min) m/z 252.37 [C$_{12}$H$_{17}$N$_3$O$_3$+H]$^+$ (100), Rt 0.83 min; HRMS m/z calc C$_{12}$H$_{18}$N$_3$O$_3$ [M+H]$^+$252.1353. found [M+H]$^+$252.1358; anal. CHN calc. C$_{12}$H$_{17}$N$_3$O$_3$. C, 57.4%; H, 6.8%; N, 16.7%. found C, 57.3%; H, 7.1%; N, 16.6%.

Procedure for the synthesis of N-(3-aminophenyl)-2-(diethylamino)acetamide (5)

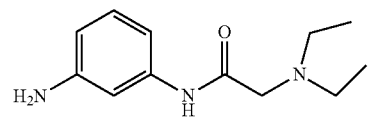

Chemical Formula: $C_{12}H_{19}N_3O$
Molecular Weight: 221.2988

2-(Diethylamino)-N-(3-nitrophenyl)acetamide 4 (0.73 g, 2.90 mmol) was dissolved in anhydrous THF (20 ml) under an atmosphere of N$_2$, then Pd/C (0.073 g) was added. The atmosphere was then saturated with H$_2$ and the mixture stirred overnight. The crude product was filtered through celite, the celite washed with EtOAc and the organic solution evaporated in vacuo. The crude was dissolved in DCM (75 ml), washed 3 times with 5N aqueous NH$_4$OH solution (50 ml), dried (MgSO$_4$), filtered and the solvent evaporated in vacuo. Compound N-(3-aminophenyl)-2-(diethylamino)acetamide 5 was obtained as a yellow oil (0.58 g, 90%) without requiring any further purification; Rf 0.44 [5% MeOH in DCM]; $\delta_H$ (CDCl$_3$, 400 MHz) 9.28 (1H, s, NH), 7.26-7.20 (1H, m, ArH), 7.07 (1H, t, J=8.0 Hz, ArH), 6.74-6.72 (1H, m, ArH), 6.43-6.40 (1H, m, ArH), 3.71 (2H, broad s, NH$_2$), 3.11 (2H, s, CH$_2$), 2.65-2.59 (4H, m, 2×CH$_2$), 1.69 (6H, t, J=7.2 Hz, 2×CH$_3$); $\delta_C$ (CDCl$_3$, 100 MHz) 169.95 (C=O), 147.27 (Ar—C), 138.64 (Ar—C), 129.61 (Ar—CH), 110.74 (Ar—CH), 109.17 (Ar—CH), 105.92 (Ar—CH), 58.14 (CH$_2$), 48.79 (2×CH$_2$), 12.39 (2×CH$_3$); HRMS m/z calc. C$_{12}$H$_{20}$N$_3$O [M+H]$^+$222.1601. found [M+H]$^+$ 222.1694.

Procedure for the synthesis of N-(3-azidophenyl)-2-(diethylamino)acetamide (6)

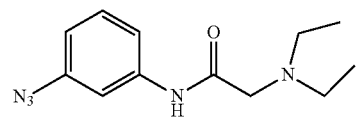

Chemical Formula: $C_{12}H_{17}N_5O$
Molecular Weight: 247.2963

N-(3-Aminophenyl)-2-(diethylamino)acetamide 5 (0.52 g, 2.35 mmol) was dissolved in THF (6 ml), and cooled in an ice bath. The resulting stirred mixture was treated sequentially with concentrated aqueous HCl (1.08 ml, 12.92 mmol), then with $^t$BuONO (0.61 g, 5.87 mmol). The reaction was stirred in an ice bath for 1.5 hours and after that time NaN$_3$ (0.46 g, 7.05 mmol) was added, followed by careful addition of water, until the reaction ceased to effervesse. The reaction was allowed to warm to room temperature and stirred overnight. The mixture was carefully neutralised with saturated aqueous NaHCO$_3$ solution and THF was evaporated in vacuo. The aqueous solution was extracted three times with EtOAc (75 ml), dried (MgSO$_4$), filtered and the solvent evaporated in vacuo, to give N-(3-azidophenyl)-2-(diethylamino)acetamide 6 as a dark brown oil (0.56 g, 85%) without requiring any further purification; Rf 0.24 [10% MeOH in DCM]; IR (film): 3279.67, 2934.63, 2110.57, 1687.86, 1515.73 cm$^{-1}$; $\delta_H$ (CDCl$_3$, 400 MHz) 9.43 (1H, s, NH), 7.41 (1H, m, ArH), 7.30-7.23 (2H, m, 2×ArH), 6.76 (1H, td, J$_1$=8.0, J$_2$=2.0 Hz, ArH), 3.13 (2H, s, CH$_2$), 2.64 (4H, m, 2×CH$_2$), 1.08 (6H, m, 2×CH$_3$); $\delta_C$ (CDCl$_3$, 100 MHz) 170.25 (C=O), 140.95 (Ar—C), 139.18 (Ar—C), 130.14 (Ar—CH), 115.60 (Ar—CH), 114.48 (Ar—CH), 109.96 (Ar—CH), 58.11 (CH$_2$), 48.92 (2×CH$_2$), 12.40 (2×CH$_3$); LC-MS (5 min) m/z 248.49 [C$_{12}$H$_{17}$N$_5$O+H]$^+$ (25), 220.07 [(C$_{12}$H$_{17}$N$_5$O+H)-28]$^+$ (40) Rt 2.05 min; HRMS m/z calc. C$_{12}$H$_{18}$N$_5$O [M+H]$^+$ 248.1506. found [M+H]$^+$ 247.1498.

Procedure for the synthesis of N,N'-((4,4'-(Naphthalene-2,7-diyl)bis(1H-1,2,3-triazole-4,1-diyl))bis(3,1-phenylene))bis(2-(diethylamino)acetamide) (CL67)

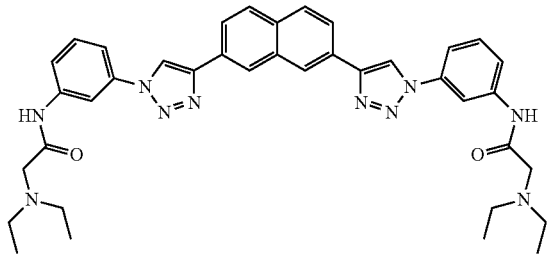

Chemical Formula: C$_{38}$H$_{42}$N$_{10}$O$_2$
Molecular Weight: 670.8059

2,7-diethynylnaphthalene 3 (20 mg, 0.11 mmol) was dissolved in H$_2$O (1.5 ml) and $^t$BuOH (1.5 ml), followed by the addition of N-(3-azidophenyl)-2-(diethylamino)acetamide 6 (84 mg, 0.34 mmol), and the catalytic mixture of CuSO$_4$ 5H$_2$O (2 mg, 0.005 mmol) and sodium ascorbate (11 mg, 0.05 mmol). An extra catalyst, bathophenanthrolinedispufonic acid disodium salt hydrate (click catalyst', 6 mg, 0.01 mmol) was added and the resulting mixture was heated under microwave irradiation for 15 minutes at 110° C. and was monitored by LC-MS [Solvents: A=H$_2$O, 0.1% formic acid; B=CH$_3$CN, 0.1% formic acid. 0 min (95% A, 5% B), 1 min (95% A, 5% B), 3 min (50% A, 50% B), 5 min (95% A, 5% B)]. After completion, the reaction was evaporated in vacuo and the brown solid crude obtained (126 mg) was purified by HPLC [(Solvents: A=H$_2$O, 0.1% formic acid; B=CH$_3$CN, 0.1% formic acid. 0 min (100% A, 0% B), 6 min (70% A, 30% B), 19 min (60% A, 40% B)]. N,N'-((4,4'-(Naphthalene-2,7-diyl)bis(1H-1,2,3-triazole-4,1-diyl))bis(3,1-phenylene))bis(2-(diethylamino)acetamide). (CL67) was obtained as a beige solid (quantitative, the yields was calculated measuring the integrals of the crude LC-MS peaks); HPLC Rt 12.06 minutes, purity 97%; mp 97-99° C.; $\delta_H$ (d$_6$-DMSO, 400 MHz) 10.01 (2H, s, 2×NH), 9.44 (2H, s, 2×C=CH), 8.61 (2H, s, 2×ArH), 8.44-8.43 (2H, m, 2×ArH), 8.17-8.09 (4H, m, 4×ArH), 7.82-7.80 (2H, m, 2×ArH), 7.68-7.65 (2H, m, 2×ArH), 7.61-7.57 (2H, m, 2×ArH), 3.23 (4H, s, 2×CH$_2$), 2.64 (8H, quartet, J=7.2 Hz, 4×CH$_2$), 1.05 (12H, t, J=7.2 Hz, 4×CH$_3$); $\delta_C$ (d$_6$-DMSO, 100 MHz) 170.39 (2×C=O), 147.13 (2×C=CH), 139.76 (2×Ar—C), 136.84 (2×Ar—C), 133.25 (Ar—C), 132.36 (Ar—C), 130.22 (2×Ar—CH), 128.61 (2×Ar—C), 128.36 (2×Ar—CH), 123.97 (2×Ar—CH), 123.89 (2×Ar—CH), 120.15 (2×C=CH), 119.30 (2×Ar—CH), 114.74 (2×Ar—CH), 110.88 (2×Ar—CH), 57.25 (2×CH$_2$), 47.81 (4×CH$_2$), 11.83 (4×CH$_3$); HRMS m/z calc. C$_{38}$H$_{43}$N$_{10}$O$_2$ [M+H]$^+$ 671.3571. found [M+H]$^+$ 671.3594.

Example 2

Cell Assays

Materials and Methods

Cells and Reagents

A498 human renal, 786-0 human renal, MCF-7 human breast, Mia-Pa-Ca human pancreatic, Panc-1 human pancreatic, and PC-3 human prostate cancer cells were obtained from American Type Culture Collection (Rockville, Md.). Human RCC4 and RCC4/VHL cells were obtained from Professor P. Maxwell (University College London, UK) [1]. RCC4 cells lack pVHL therefore express constitutively high levels of HIF-1α. These cells were stably transfected with a wild-type pVHL gene, as previously described [1]. All cells were grown in humidified 95% air, 5% CO$_2$ at 37° C. in Dulbecco's modified Eagle's medium (DMEM), RPMI or MEM medium supplemented with 10% fetal bovine serum (FBS) and 2 mM L-Glutamine according to advice from ATCC (all reagents were obtained from Gibco, Invitrogen, UK). HIF-1α and HIF-2α antibodies were obtained from BD Transduction Labs, AKT antibody was obtained from Cell Signalling Biotechnology, and lamin NC, actin, HIF-1β, HSP-90, and Raf-1 antibodies were from Santa Cruz Biotechnology.

Hypoxia Treatments

Culture flasks were incubated for various times at 37° C. in humidified air, 5% CO$_2$ (normoxia) or 1% O$_2$, 5% CO$_2$, 94% N$_2$ (hypoxia) using an InVivo Hypoxia Workstation 400 with a Ruskin hypoxic gas mixer (Biotrace International). After incubation, cells were washed twice with cold PBS equilibrated with the same gas mixture. In some studies, medium was removed at the end of incubation and stored at 80° C. for measurement of vascular endothelial growth factor (VEGF) levels.

Growth Inhibition Assays

Short-term antiproliferative activity was evaluated by the sulforhodamine B assay, and calculated as IC$_{50}$ values for 96 hr exposure [6].

Western Blotting

Western blotting was performed as described previously [7]. Blots were quantified using ImageQuant software (Molecular Dynamics). Nuclear and cytoplasmic extracts were prepared using NE-PER Nuclear and Cytoplasmic Extraction Reagents (Pierce Biotechnology).

Luciferase Reporter Assays

A pGL3 firefly luciferase reporter plasmid containing the phosphoglycerate kinase hypoxia-responsive element was supplied by Professor P. Maxwell (University College London, UK) [1]. The empty pGL3 control plasmid and the pRL-CMV Renilla luciferase plasmids were obtained from Promega. Cells were transfected with HIF-1 reporter plasmid (HRE), or pGL3 control plasmid, and pRL-CMV Renilla luciferase plasmid using LipoTAXI (Stratagene) and 24 h later were exposed to normoxia or hypoxia for the required time, with or without CL67. Firefly and Renilla luciferase activities were measured using the Dual Luciferase Reporter Assay System (Promega) according to the manufacturer's instructions.

VEGF Measurements

Approximately 10$^7$ cells were treated with CL67 as required. 1 mL of cell culture medium was removed and cleared using centrifugation at 1500 rpm, 4° C., 3 minutes. The supernatant was stored at −80° C. until assay. The amount of VEGF was determined using a human VEGF ELISA kit that measure $VEGF_{165}$ and $VEGF_{121}$ isoforms (R&D Systems, Minneapolis, Minn.). reacts with mouse erythropoietin, and mouse erythropoietin as a standard.

Reverse Transcriptase PCR (RT-PCR)

Total RNA was isolated from approximately $10^7$ cells using the RNeasy kit (Qiagen, Crawley, UK) according to the manufacturer's protocol. HIF-1α transcripts were quantified using two-step, quantitative real time PCR (qRTPCR). First-strand cDNA synthesis was performed for each sample with a Protoscript M-MuLV Taq RT-PCR kit (New England Biolabs, MA, USA) using 1 μg total RNA and oligo-dT primers. qPCR was performed using Stratagene Brilliant III SYBR Green master mix in a Stratagene MX-3000P instrument (Agilent, Tex., USA) according to the manufacturer's instructions using 2 ng input cDNA and primers at 300 nM. Duplicate biological samples were measured in duplicate for each gene, then fold-regulation relative to the untreated control was determined using the Relative Expression Software Tool-384, version 2 [9]. Samples were normalised to β-actin. Differences in PCR efficiency were normalised using relative standard curves of cDNA pooled from all samples. P-values were determined for 2000 randomisations.

Xenograft Studies

Animals were housed in groups of five at 19° C. to 23° C., with a 12-hour light-dark cycle, and fed with a conventional diet. Experimental work was carried out in accordance with UK Home Office regulations.

Dose Ranging

A dose range assay was performed in female CD1 mice, with an initial mean weight of 25 g (Harlan UK Ltd,). CL67 was dissolved in sterile $dH_2O$ and administered intra-peritoneally to the mice (n=2). The body weight was recorded daily and the animals were observed for clinical symptoms [8]. The starting dose of 0.08 mg $kg^{-1}$ was increased step-wise up to 10 mg $kg^{-1}$, being this the solubility limit of the drug in aqueous media.

In Vivo Efficacy in 786-0 Xenografts

Five to six weeks old immunodeficient Swiss nude mice (Charles River UK Ltd) were maintained in individually ventilated caging (IVC) systems. Tumors were established in the right flank of the mice, by subcutaneous injection of $1\times10^7$ 786-0 cells in a mixture of 50:50 (v/v) medium and Matrigel® (BD Biosciences). Tumour development was monitored by serial calliper measurement with tumour volume calculated as $$V = \frac{d^3\pi}{6}.$$

4 weeks after inocculation (median tumour volume of ~150 $mm^3$) animals were randomised into 6 groups (n=4). One of the group was used as a control (untreated) and the rest of the mice were given CL67 intraperitoneally at a dose of 10 mk/kg. Treated animals were sacrificed at 2 h, 4 h, 6 h, 16 h and 24 h after injection. The tumour tissue was immediately excised and placed into 250 μL lysis buffer. The tissue was homogenised and incubated on ice for 1 hour. The supernatant was then collected by centrifugation (15,000 rpm, 10 min, 4° C.) on a bench top centrifuge. Supernatants were stored at −80° C. until assay. The plasma and main organs of the mice (heart, lungs, liver, spleen and kidneys) were also collected and snap-frozen in liquid nitrogen for further analysis.

Results

Figure 4:
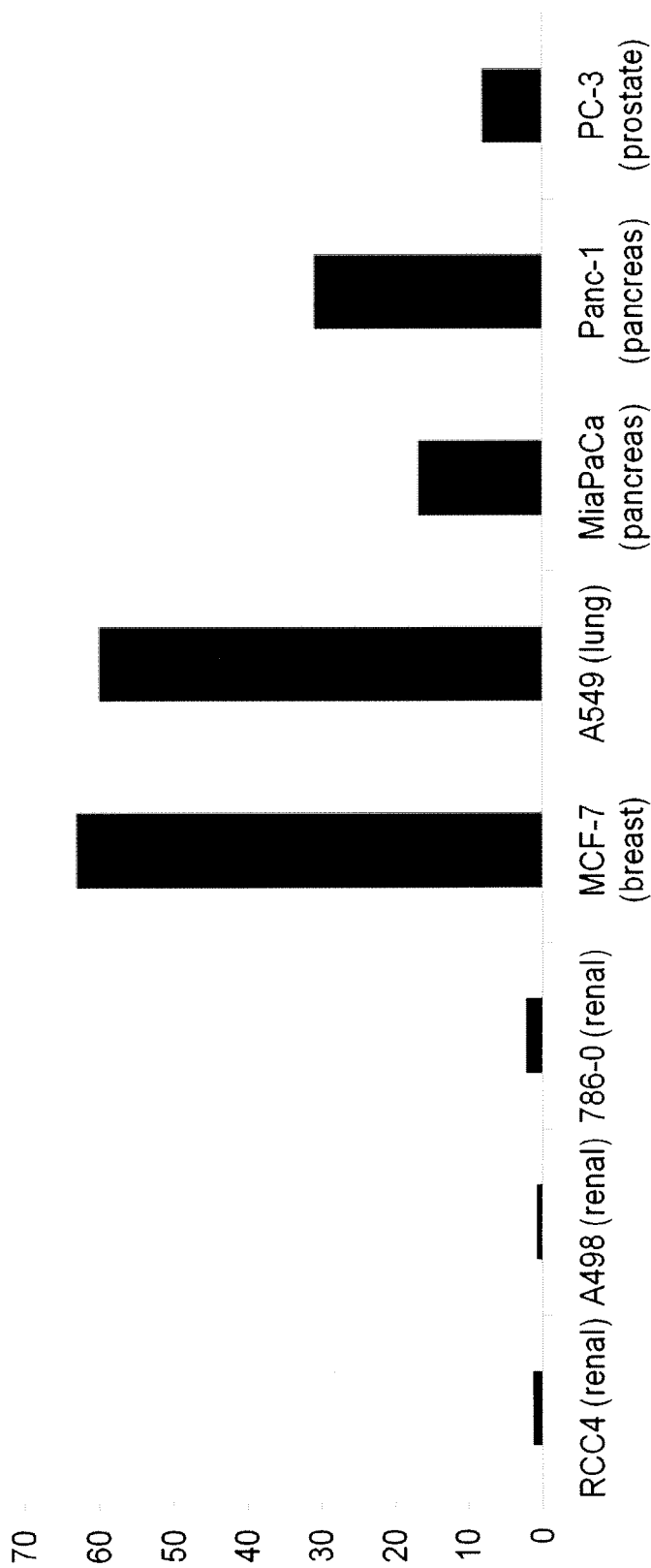
FIG. 4 illustrates how CL67 is a potent inhibitor of renal carcinoma cells compared to other cell types.

FIG. 4 shows that CL67 is a potent inhibitor of renal carcinoma cells compared to other cancer cell types.

In this experiment, cells were incubated for 96 h with CL67 (10 nM to 100 μM) in normoxia (20% oxygen). The sulphorhodamine B (SRB) assay was then performed and the concentration required to inhibit cell growth by 50% (IC50) was determined. Renal cancer cells showed enhanced sensitivity to inhibition of cell growth compared to other cancer cell lines (breast, pancreatic, prostate).

FIG. 5 shows that CL67 inhibits HIF-1α and HIF-2α protein in a dose and time dependent manner but does not affect levels of HIF-1β. In these experiments, RCC4 (A) or 786-0 (B) cells were incubated in either normoxia (RCC4) or hypoxia (1% oxygen; 786-0) for 4 h with the doses of CL67 indicated. For FIG. 5C) RCC4 cells were treated with CL67 (5×IC50) for the times indicated. Cells were then lysed and Western blotting was performed probing for HIF-1α, HIF-2α, HIF-1β, or lamin NC (as a loading control). CL67 inhibited both HIF-1α and HIF-2α but did not affect levels of HIF-1β.

FIG. 6 shows that CL67 inhibits HIF-1 transactivation and down-stream target genes.

In FIG. 6(A) RCC4 cells were co-transfected with either a vector expressing luciferase under the control of multiple copies of the hypoxia response element (HRE; kindly donated by G. Mellillo, NCI) or an empty vector control (pGL3) in addition to a vector expressing renilla luciferase (to control for transfection efficiency). Cells were then exposed to either normoxia or hypoxia (1% oxygen) in the presence of the concentrations of CL67 shown for 4 h. Luciferase activity was then measured using the Promega Dual Luciferase assay Kit and results are expressed as a percentage of the activity of untreated, normoxic cells. In FIG. 6B) RCC4 cells were exposed to CL67 (5×IC50, or the dose indicated) for 4 h (or the time indicated). VEGF levels were then measured in the medium using ELISA. CL67 inhibited HIF-1 transactivation and VEGF levels demonstrating that CL67 inhibits the HIF-1 pathway.

FIG. 7 shows that CL67 inhibits HIF-1α in a pVHL independent manner. RCC4 cells (lacking pVHL) (A) and RCC4VHL (B) cells (RCC4 cells stably transfected with pVHL) were incubated with 0, 1, 5 or 10×IC50 doses of CL67 for the times indicated in the presence of normoxia (N; 20% oxygen) or hypoxia (H; 1% oxygen). Cells were then lysed and Western blotting was performed probing for HIF-1α and lamin (as a loading control). HIF-1α protein was inhibited in both cell lines indicating that CL67 inhibits HIF-1α protein by a pVHL independent mechanism.

FIG. 8 shows that CL67 inhibits the HIF pathway independently of oncogenic signalling pathways such as MAPK/PI3K. RCC4 and RCC4VHL cells were treated with CL67 (5×IC50) for the times indicated under normoxic conditions (20% oxygen). Cells were then lysed and Western blotting was performed. Probing for HSP-90, Raf-1, AKT and actin (as a loading control). No differences in expression of HSP90, Raf-1 or AKT were detected.

FIG. 9 shows that CL67 inhibits HIF-1α by inhibiting transcription of HIF-1α. RCC4 cells were treated with CL67 for 4 h under normoxia with the doses shown. Cells were then lysed and RNA was prepared using a Qiagen RNeasy kit. RT PCR was then performed to determine relative levels of HIF- 1α mRNA in each sample. Results are presented as relative expression of HIF-1α mRNA compared to untreated control cells. These data show that CL67 inhibits formation of HIF-1α mRNA. Therefore it is likely that CL67 inhibits the HIF pathway via the G-quadruplex transcriptional control element, although further experiments are needed to confirm this hypothesis.

From the data above, we can infer that CL67, an example of a compound according to this invention, inhibits G-quadruplex sequences in oncogenic promoters and selectively inhibits renal carcinoma cell growth and viability.

The compound acts via the HIF pathway.

REFERENCES

1. Maxwell P H et al; The tumour suppressor protein VHL targets hypoxia-inducible factors for oxygen-dependent proteolysis. Nature, 399(6733):271-5, 1999.
2. Krieg, M. et al; Up-regulation of hypoxia-inducible factors HIF-1a and HIF-2a under normoxic conditions in renal carcinoma cells by von Hippel-Lindau tumor suppressor gene loss of function. Oncogene, 19: 5435-5443, 2000.
3. Turner, K J. et al; Expression of hypoxia-inducible factors in human renal cancer: relationship to angiogenesis and to the von Hippel-Lindau gene mutation. Cancer Res, 62: 2957-2961, 2002.
4. Maxwell, P H. et al; Hypoxia-inducible factor-1 modulates gene expression in solid tumors and influences both angiogenesis and tumor growth. Proc Natl Acad Sci USA, 94: 8104-8109, 1997.
5. De Armond R. et al; Evidence for the presence of a guanine quadruplex forming region within a polypurine tract of the hypoxia inducible factor 1alpha promoter. Biochemistry, 44(49):16341-50, 2005.
6. Fernando H, et al; A conserved quadruplex motif located in a transcription activation site of the human c-kit oncogene. Biochemistry 2006; 45:7854-7860.
7. Koh M Y et al; Molecular mechanisms for the activity of PX-478, an antitumor inhibitor of the hypoxia-inducible factor-1alpha. Mol Cancer Ther. 2008 January; 7(1):90-100.
8. Morton D B, et al; Guidelines on the recognition of pain, distress and discomfort in experimental animals and a hypothesis for assessment. Vet Rec. 1985, 116(16):431-6.
9. Pfaffl, M. A new mathematical model for relative quantification in real-time RT-PCR. Nucleic Acids Res. 2001 29:e45.
10. Sparapani et al; Rational Design of Acridine-based ligands with selectivity for human telomeric quadruplexes. J. Am. Chem. Soc 2010, 132, 12263-12272.
11. Lombardo et al; structure-based design of selective high-affinity telomeric quadruplex-binding ligands, Chem. Commun., 2010, 46, 9116-9118.

The invention claimed is:

1. A compound of formula I:

(I)

wherein $Ar^1$ is a bicyclic aryl or heteroaryl, which may be optionally substituted;
X and Y are each independently a group of formula II:

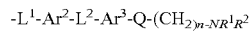

$L^1$ and $L^2$ are each independently selected from $NR^3$, $C_2H_2$, $CH_2$, —O—, —S— and a bond;
$Ar^2$ and $Ar^3$ are independently optionally substituted $C_5$ or $C_6$ aryl or heteroaryl;
Q is selected from $NH(C=O)$, $NR^3$, S, O;
n is an integer from 1 to 5;
$R^1$ and $R^2$ are optionally substituted and are independently hydrogen, $C_{1-7}$ alkyl, $C_{3-20}$ heterocyclyl, or $C_{5-20}$ aryl, or $R^1$ and $R^2$, taken together with the nitrogen atom to which they are attached, form a heterocyclic ring having from 3 to 8 ring atoms;
$R^3$ is H or $C_{1-7}$ alkyl.

2. A compound according to claim 1, wherein $Ar^1$ is a naphthalene ring.

3. A compound according to claim 2, wherein X and Y are substituted 2,7 on the naphthalene ring.

4. A compound according to claim 1 wherein X is identical to Y.

5. A compound according to claim 1, wherein Q is

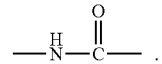

6. A compound according to claim 1, wherein n is 1 or 2.

7. A compound according to claim 1, wherein each $Ar^2$ is triazole.

8. A compound according to claim 1, wherein each $Ar^3$ is phenyl.

9. A compound according to claim 1, wherein each $L^1$ is a bond and/or each $L^2$ is a bond.

10. A compound according to claim 1, wherein $R^1$ and $R^2$ are each independently $C_{1-7}$ alkyl, which is optionally substituted, wherein each —$NR^1R^2$ is independently selected from —$N(Me)_2$, —$N(Et)_2$, —$N(nPr)_2$, —$N(iPr)_2$, —$N(nBu)_2$, or —$N(tBu)_2$, or wherein in each group $NR^1R^2$ $R^1$ and $R^2$, taken together with the nitrogen atom to which they are attached, form a heterocyclic ring having from 3 to 8 ring atoms, which heterocyclic ring may saturated, partially unsaturated, or

SEQUENCE LISTING

<160> NUMBER OF SEQ ID NOS: 1

<210> SEQ ID NO 1
<211> LENGTH: 31
<212> TYPE: DNA
<213> ORGANISM: Homo sapiens

<400> SEQUENCE: 1 gcgcgggggag gggagagggg gcgggagcgc g                                    31 fully unsaturated, and is optionally substituted, wherein $R^1$ and $R^2$, taken together with the nitrogen atom to which they are attached, form a saturated heterocyclic ring having from 3 to 8 ring atoms, wherein only one of said ring atoms is nitrogen, and all others are carbon, and which heterocyclic ring is optionally substituted.

11. A compound according to claim 10, wherein $R^1$ and $R^2$, taken together with the nitrogen atom to which they are attached form a cyclic amino group of the following formula, wherein q is an integer from 2 to 7, and wherein said group is optionally substituted:

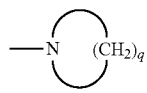

wherein each group —$NR^1R^2$, is one of the following cyclic amino groups, and is optionally substituted:

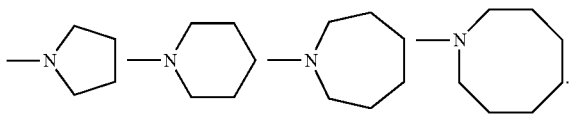

12. A compound according to claim 11, wherein said cyclic amino group is substituted with one or more substituents selected from $C_{1-7}$ alkyl, $C_{3-20}$ aryl, hydroxy, and $C_{1-7}$ hydroxyalkyl.

13. A compound according to claim 10, wherein in each $NR^1R^2$ group $R^1$ and $R^2$, taken together with the nitrogen atom to which they are attached, form a saturated heterocyclic ring having from 3 to 8 ring atoms, wherein said ring has at least two heteroatoms selected from nitrogen, oxygen, and sulfur, which heterocyclic ring is optionally substituted, wherein the group —$NR^1R^2$, is one of the following cyclic amino groups, and is optionally substituted:

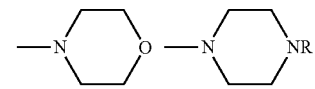

wherein R is hydrogen, $C_{1-7}$ alkyl, $C_{3-20}$ heterocyclyl, or $C_{5-20}$ aryl.

14. A compound according to claim 1 of formula

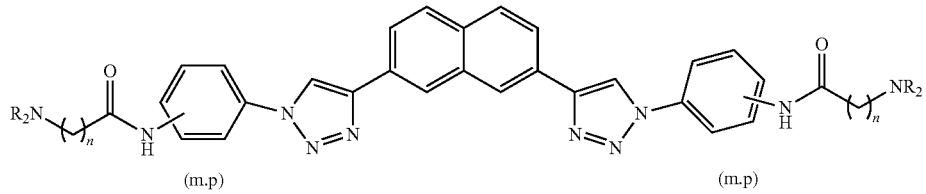

wherein n is an integer 1 or 2; and
each R group is independently $C_{1-4}$ alkyl, $C_{4-5}$ heterocyclyl or $C_{3-5}$ heteroaryl, or the two R groups on each nitrogen, taken together with the nitrogen to which they are attached, form a heterocyclic ring having 5-7 ring atoms.

15. A pharmaceutical composition comprising a compound according to claim 1, or a pharmaceutically acceptable salt, ester, amide, solvate, hydrate or protected form thereof, and a pharmaceutically acceptable diluent or carrier.

16. A method of inhibiting the HIF gene in vitro or in vivo, comprising contacting a cell with an effective amount of compound according to claim 1, whereby the HIF gene is inhibited.

17. A method of regulating cell proliferation in vitro and/or in vivo, by inhibiting the HIF gene comprising contacting a cell with an effective amount of compound according to claim 1, whereby cell proliferation is regulated, whereby the HIF gene is inhibited and therefore cell proliferation is regulated.

18. A method for the treatment of a proliferative condition associated with HIF gene inhibition, comprising administering to a subject suffering from said proliferative condition a therapeutically effective amount of a compound according to claim 1.

19. A method according to claim 18, wherein the proliferative condition is cancer.

20. A method according to claim 19, wherein the proliferative condition is renal cancer.

* * * * *